US008479577B2

(12) United States Patent
Ganin (10) Patent No.: US 8,479,577 B2
(45) Date of Patent: Jul. 9, 2013

(54) IN-LINE INSPECTION TOOL FOR PIPELINE INTEGRITY TESTING

(75) Inventor: Yevgeniy Vladimirovich Ganin, Kolomna (RU)

(73) Assignee: Weatherford/Lab, Inc., Houston, TX (US)

(*) Notice: Subject to any disclaimer, the term of this patent is extended or adjusted under 35 U.S.C. 154(b) by 440 days.

(21) Appl. No.: 12/701,953

(22) Filed: Feb. 8, 2010

(65) Prior Publication Data

US 2010/0199767 A1 Aug. 12, 2010

Related U.S. Application Data

(60) Provisional application No. 61/150,884, filed on Feb. 9, 2009.

(51) Int. Cl.
*G01N 29/04* (2006.01)
(52) U.S. Cl.
USPC .......................................................... 73/623
(58) Field of Classification Search
USPC ............................................................ 73/623
See application file for complete search history.

(56) References Cited

U.S. PATENT DOCUMENTS

| 4,092,868 | A | 6/1978 | Thompson et al. |
| 4,100,809 | A | 7/1978 | Bobrov et al. |
| 4,301,684 | A | 11/1981 | Thompson et al. |
| 5,460,046 | A | 10/1995 | Maltby et al. |
| 5,537,876 | A | 7/1996 | Davidson et al. |
| 5,907,100 | A | 5/1999 | Cook |
| 6,250,163 | B1 | 6/2001 | MacLauchlan et al. |
| 7,406,873 | B2 | 8/2008 | Paige et al. |
| 2005/0072237 | A1 | 4/2005 | Paige et al. |
| 2009/0139337 | A1 | 6/2009 | Owens et al. |
| 2009/0193899 | A1* | 8/2009 | Panetta et al. ............... 73/622 |

FOREIGN PATENT DOCUMENTS

CA 2592094 7/2006

OTHER PUBLICATIONS

Thomas Beuker et al. "SCC Detection and Coating Disbondment Detection Improvements Using the High Resolution Emat Ili-Technology", Proceedings of IPC 2004, 5th International Pipeline Conference, 2004, Calgary, Alberta, Canada.
F. B. Cegla "Ultrasonic Crack Monitoring Using SH Waves in extreme and inaccessible environments", 17th World Conference on Nondestructive Testing, 2008, Shanghai, China.
Hirao Laboratory-English ver.—"EMAT (Electromagnetic acousti transducer)", http://www-ndc.me.es.osaka-u-ac.jp/pmwiki e/pmwiki.php?n=Main.EMATs, 2008, Osaka University Hirao Laboratory.
Lopez, Borja, "Weld Inspection with EMAT Using Guided Waves", May 2008, Ndt.net—The e-Journal of Nondestructive Testing.
Pipeline & Gas Journal's 2005 Capabilities Guide, Rosen Detects Crack-like Defects in Gas Pipeline, www.pipelineandgasjournal.com, Jul. 2005.

\* cited by examiner

*Primary Examiner* — Hezron E Williams
*Assistant Examiner* — Gregory J Redmann
(74) *Attorney, Agent, or Firm* — Wong, Cabello, Lutsch, Rutherford & Brucculeri LLP (57) ABSTRACT

Apparatus and methods are provided for non-destructive in-line pipeline inspection utilizing electromagnetic acoustic transducer (EMAT) technology wherein the EMATs are arrayed circumferentially in a belt around the body of the tool and wherein the EMAT belt includes a plurality of EMAT clusters, each cluster including a transmitting EMAT essentially sandwiched between a pair of receiving EMATs. The EMAT arrangement enables a single receiving EMAT to monitor both the test signal and the returning reflection from the pipewall defect thus providing each signal with its own internal reference. The number of transducers and their positional relationship limits the generation of interference signals, is conservative in power consumption, and provides a tool having enhanced negotiability through the pipeline.

28 Claims, 10 Drawing Sheets

IN-LINE INSPECTION TOOL FOR PIPELINE INTEGRITY TESTING

CROSS REFERENCE TO RELATED APPLICATIONS

This application claims priority based on U.S. Provisional Application Ser. No. 61/150,884 filed Feb. 9, 2009, which is incorporated herein by reference in its entirety.

FIELD OF THE INVENTION

This invention relates to in-line inspection of pipelines for structural and/or coating defects and more particularly to inspection of electrically conductive pipes employing in-line inspection pigs that utilize electromagnetic acoustic transducer technology.

BACKGROUND OF THE INVENTION

Without limiting the scope of the invention, its background is described in connection with novel apparatus and methods for non-destructive pipeline inspection. Pipelines require periodic testing to insure the absence of defects that may ultimately result in loss of product or catastrophic pipeline failure. Pipeline defects may include loss of coatings, corrosion, stress corrosion cracking (SCC), and circumferential and axial flaws. Non-destructive testing (NDT) methods include internal inspection using smart pigs that are adapted to run the length of the pipeline while conducting testing. Testing methods include physical surface analysis, corrosion testing and crack detection. Corrosion manifest as metal loss, as well as crack detection, are most typically detected by magnetic flux leakage (MFL) although ultrasound testing has also been applied to corrosion and crack detection.

Electromagnetic acoustic transducer (EMAT) technology is relative newcomer to the field of non-destructive pipeline integrity testing. EMAT technology involves the generation of ultrasonic acoustic waves in electrically and magnetically conductive materials by the combined interaction of magnetic fields together with a relatively high frequency (RF) field generated by electrical coils. The low frequency or static field generated by the magnets interacts with eddy currents in the RF field to generate ultrasonic acoustic waves caused by Lorentz forces or magnetostriction in the test material. Depending on the configuration of the electrical coil and the magnetic field, a number of different types of ultrasonic acoustic waves can be generated in the tested material including, among others, shear waves. Generated shear waves can be shear vertical (SV) or shear horizontal (SH) waves depending on the method of excitation. Excitation of SH waves may result in concomitant excitation of SV waves, which propagate in the same direction as the SH waves but at smaller amplitudes. An EMAT designed to utilize SH waves employs a row of magnets with alternating polarities that produces a shear wave whose polarization is in the plane of the surface to be tested. Defects such as corrosion or cracks in the pipeline walls create detectable reflections in the generated shear waves.

The EMAT in-line inspection method described by Paige et al. (PCT/GB02/04031, "Pipeline Inspection Pigs", published as WO03/021249 and US2005/0072237) uses rings of transmit/receive transducers wherein each ring includes two to three sets of pairs of transmitting and receiving transducers (T1, R1, T2, R2, etc), with the pairs being co-planar and evenly circumferentially spaced close to the internal surface of the pipe. All transmitting EMAT in this set are switched on simultaneously. To avoid measurement interference by ultrasound waves circulating around the circumference of the pipe, a time interval between emission of a given ultrasound wave and emission of a consequent ultrasound wave is established to be long enough for all previous ultrasound waves to have decayed by the time of emission of the next ultrasound wave. To assure unambiguity of the location of defects and to increase probability of their detection, the rings of transmit/receive transducers described in the above mentioned PCT/GB02/04031 are spaced along the axis at a distance that is long enough to exclude ultrasonic waves of one ring from being received by transducers of the adjacent ring. The transmit/receive transducers of a given ring are installed with an angular shift relative to the transmit/receive transducers of the adjacent ring. While this method has an advantage of using a small number of EMAT to ensure low power consumption and therefore maximum effective range of the in-line inspection tool, in this method the several transducers sets are shifted along the axis, resulting in an increased length of the in-line inspection tool. Moreover, the long time interval between emissions of ultrasound waves as the tool is moving through the pipeline establishes a relatively long distance along the pipeline axis between where ultrasound waves are generated and where crack-like defects can be detected thus limiting the in-line inspection length resolution along the axis of the pipe.

A further EMAT technology in-line inspection method, described by Alers et al. (CA2592094, "Device for Testing Ferromagnetic Component Walls Without Destruction of the Same", published as WO06/069684), involves transmitting EMATs generating ultrasound waves that propagate at a 10-60 degree, and preferably a 20-50 degree, angle to the direction of magnetic field. For each direction of ultrasound wave emission from each transmitting EMAT there is one corresponding receiving EMAT located some distance away from the zone of the ultrasound wave propagation according to the emission direction and which receives only ultrasound waves that are reflected from crack-like defects in the testing area. A further separate reference EMAT is employed that is located outside the testing area and which receives ultrasound waves that have traveled through the testing area. An advantage of this method of inspection is that the generated ultrasound waves, while propagating along the pipe wall, travel away from the pipe circumference where they have been generated. This arrangement avoids ultrasound wave circulation and influence on subsequent measurement of following ultrasound waves. The main disadvantage of this method is that in order to cover the whole circumference of the pipe there is a need for at least two rows of EMATs where one row forms transmitting EMATs covering the whole circumference of the pipe and the other forms receiving EMATs. The initial ultrasound wave is received with one EMAT, and the ultrasound wave reflected from a crack is received with a second EMAT. Because ultrasound waves travel away from the pipe circumference where they have been generated, a large number of EMATs are used to cover the whole circumference of the pipe. However, EMATs are the most power-consuming elements in the electronic system of such an inspection tool. Because batteries installed in a tool have limited capacity, the number of EMATs is a factor which limits hours of service of the in-line inspection tool, and therefore its maximum effective range. Having a large number of power-consuming EMATs is a factor that limits the maximum operating range of the tool.

What is needed is an EMAT inspection method and apparatus that effectively detects pipeline wall defects without signal interference but features a compact design and conservative power consumption.

BRIEF SUMMARY OF THE INVENTION

Provided herein is an electromagnetic acoustic transducer (EMAT) in-line pipeline inspection tool that provides high sensitivity, low interference and conservative power consumption in a compact arrangement of transducers that provides for a relatively short tool designed for enhanced pipeline negotiability.

In one embodiment, an EMAT pipeline inspection tool is provided that includes a tool or pig body having mounted thereon at least one pipewall magnetization element and at least one EMAT belt, wherein the EMAT belt comprises a plurality of individual EMAT Receiving/Transmitting (R/T) clusters arranged circumferentially around the tool body, each EMAT R/T cluster including one transmitting EMAT disposed between paired receiving EMATs. In one aspect, the transmitting EMATs of individual EMAT R/T clusters are adapted to generate ultrasound waves in the pipeline wall in two opposite directions. In one embodiment, the paired receiving EMATs in an individual R/T EMAT cluster are at least partly located in a zone of ultrasound wave propagation that is generated by the transmitting EMAT of the same R/T EMAT cluster. Thus, in such embodiments the EMATs of an individual cluster can be arranged to enable a single receiving EMAT to monitor both a test signal sent from the transmitting EMAT and a returning reflection from a pipewall crack-like defect, thereby providing each signal with its own internal reference.

In one embodiment, the pipewall magnetization element includes two belts of paired magnets having poles of polarity facing the internal surface of the pipewall, each of the two belts populated by paired magnets of opposite polarity to those of the other belt of magnets. The magnetization element is adapted to generate, in a pipewall, a magnetic field (B) whose orientation coincides with a direction of a longitudinal axis of the pipeline and a longitudinal axis of tool body. In such embodiments, the EMAT belt is disposed in-between the belts of magnets of opposite polarity and the transmitting EMATs of the belt have longitudinal axes that are perpendicular to the direction of ultrasound wave emission and the transmitting EMAT longitudinal axes are oriented at ($\alpha$) angle to the orientation of magnetic field (B). The receiving EMATs of such embodiments have longitudinal axes which are perpendicular to the direction of ultrasound wave reception and the receiving EMAT longitudinal axes are oriented at ($-\alpha$) angle to the orientation of magnetic field (B). In one such embodiment, the ($\alpha$) angles of the transmitting EMATs are from 3 to 20 degrees and the receiving EMATs have matching but negative ($\alpha$) angles from $-3$ to $-20$ degrees.

In one embodiment the EMATs in the R/T cluster are centered on a linear axis and the linear axis is at an angle ($\beta$) to the direction of the magnetic field (B) and a line that is perpendicular to the linear axis. In one embodiment, the ($\beta$) angle is the same for all EMAT R/T clusters in the EMAT belt. In alternative embodiments, one R/T cluster will be characterized by a linear axis at an angle ($\beta$) while the adjacent EMAT R/T cluster will be characterized by a linear axis that is at an angle ($-\beta$) to the direction of the magnetic field (B) and a line that is perpendicular to the linear axis. In such embodiments the angle of the linear axis of the R/T cluster to the direction of the magnetic field (B) and a line that is perpendicular to the linear axis varies alternates to be ($\beta$) for one cluster, ($-\beta$) for the next cluster, ($\beta$) for the next cluster and so on in a circle around the tool body. In certain of such embodiments, at least one receiving EMAT from a given R/T cluster is directed with one side towards a transmitting EMAT belonging to an adjacent R/T EMAT cluster, thus permitting said receiving EMAT to receive an initial ultrasound wave from the transmitting EMAT of the adjacent cluster and act as a reference EMAT to the adjacent cluster.

BRIEF DESCRIPTION THE DRAWINGS

For a more complete understanding of the present invention, including features and advantages, reference is now made to the detailed description of the invention along with the accompanying figures.

DETAILED DESCRIPTION OF THE INVENTION

While the making and using of various embodiments are discussed in detail below, it should be appreciated that the present invention provides many applicable inventive concepts which can be employed in a wide variety of specific contexts. The specific embodiments discussed herein are merely illustrative of specific ways to make and use the invention and do not delimit the scope of the invention.

An in-line inspection tool utilizing EMAT technology is equipped with transmitting and receiving EMATs in particular arrays that generate excited waves that propagate in helical curves around the axis of the pipeline to be tested. Because the waves do not circulate around the axis as do the waves of prior art devices, interference between wave cycles is minimized whether utilizing magnetostriction or Lorentz forces. Transmitting EMATs generate ultrasound waves in the pipe wall which propagate around the circumference transversely to the pipeline axis. If, for example, there is a longitudinal crack on the propagation path of a wave, the wave is reflected from it, and receiving EMATs receive such reflected waves. Measurement of the time interval between emission of an ultrasound wave and reception of its corresponding reflected wave makes it possible to determine the distance from the EMATs to the crack, and therefore its location in the pipe. The number of transducers, their positional relationship and switching-on sequence should desirably balance the need to detect defects with high probability against undesirable generation of interfering signals and an excessive over-all power consumption. The EMAT tool provided herein delivers the required sensitivity, low interference and conservative power consumption in a compact arrangement of transducers that provides for a relatively short tool designed for enhanced pipeline negotiability.

One significant advantage of EMAT technology over simple ultrasound is that liquid coupling with the material to be tested is not required. EMAT is able excite and detect ultrasonic vibrations in metals across an air gap. However, regardless of their source, generated ultrasound waves decay poorly in the pipe wall and can repeatedly circulate around the circumference of the pipe. Thus, the positional relationship of EMATs and their switching-on sequence preferably excludes ultrasound waves intended to be received by associated receiving EMATs from entering the reception zone of other receiving EMATs of the transducer array. Efforts to avoid signal interference by longitudinal spacing have adversely affected the negotiability of such inspection tools.

The present inventor has provided several embodiments of in-line EMAT inspection tools that are compact and efficient in power utilization while avoiding ultrasound wave interference. The various arrangements of EMATs provided herein, wherein clusters of EMATs include a transmitting EMAT surrounded by a pair of specially placed receiving EMATs, allows a single belt of EMAT clusters to be used. This single EMAT belt arrangement determines lower power consumption by the electronics. Where the device is powered by on-board batteries, the lower power consumption increases the maximum operating range of the tool. Furthermore, using the disclosed EMAT arrangement, which uses only one belt of EMATs with spacing between adjacent transmitting EMATs and uses the same EMAT to receive both the initial SH wave and a reflected wave from a crack, it is possible to avoid the influence of differences in gaps between different EMATs and the pipeline wall on crack depth determination.

By the disclosed novel EMAT arrangement, it is possible to arrange testing areas in the pipe wall immediately above the EMAT belt. However, the size of the testing area for each transmitting EMAT is not limited by its size but depends on the established angle between the direction of ultrasound wave emission and the plane of the pipe cross-section, as well as the positional relationship of transmitting and receiving EMATs. Using only one belt of EMAT, including clusters of R/T EMAT that each include a transmitting EMAT sandwiched between a pair of receiving EMATs, allows for excluding the circulation of interfering ultrasound waves around the circumference of a pipe. Contrary to existing EMAT pipeline inspection tools, the disclosed arrangement makes it possible to probe the whole pipe circumference clockwise and anticlockwise using one belt of EMAT, which thus makes it possible to use data correlation to enhance efficiency of crack-like defects identification while data processing.

Example 1

Figure 1:
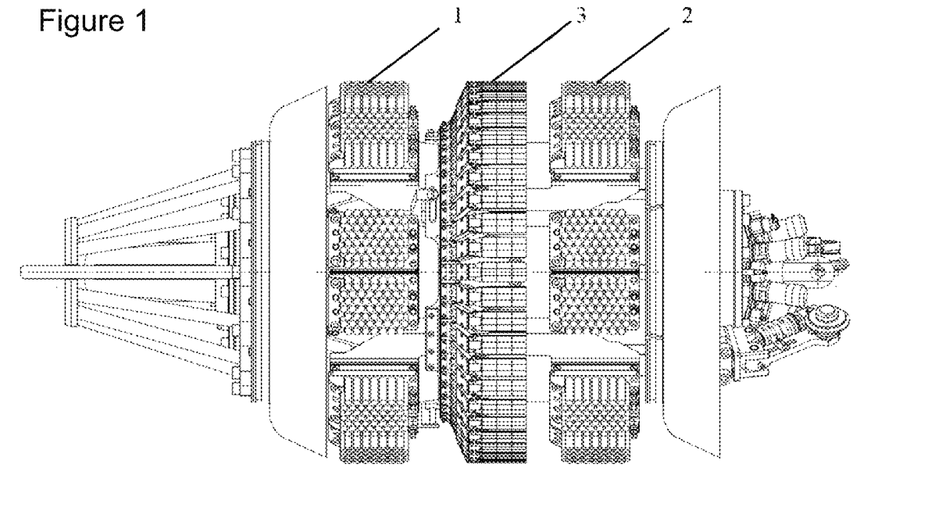
FIG. 1 depicts one embodiment of an EMAT in-line pipeline inspection tool including a potential arrangement of magnets and a circumferential belt of EMATs.

In one embodiment of an in-line inspection tool, the tool includes a body with axial symmetry that is provided with electronics for tool control and processing of measurement data. The tool includes pipe wall magnetization elements fitted on the body. As depicted in FIG. 1, the magnetization elements include belts of magnets (1) and (2) of opposite polarity wherein the poles of opposite polarity face the internal surface of a pipe. An EMAT belt (3) is installed in-between the belts of magnets of opposite polarity. The magnets (1) and (2) and EMAT array (3) are adapted to pass lightly against the internal surface of a pipeline while the inspection tool travels through the pipeline.

Figure 2:
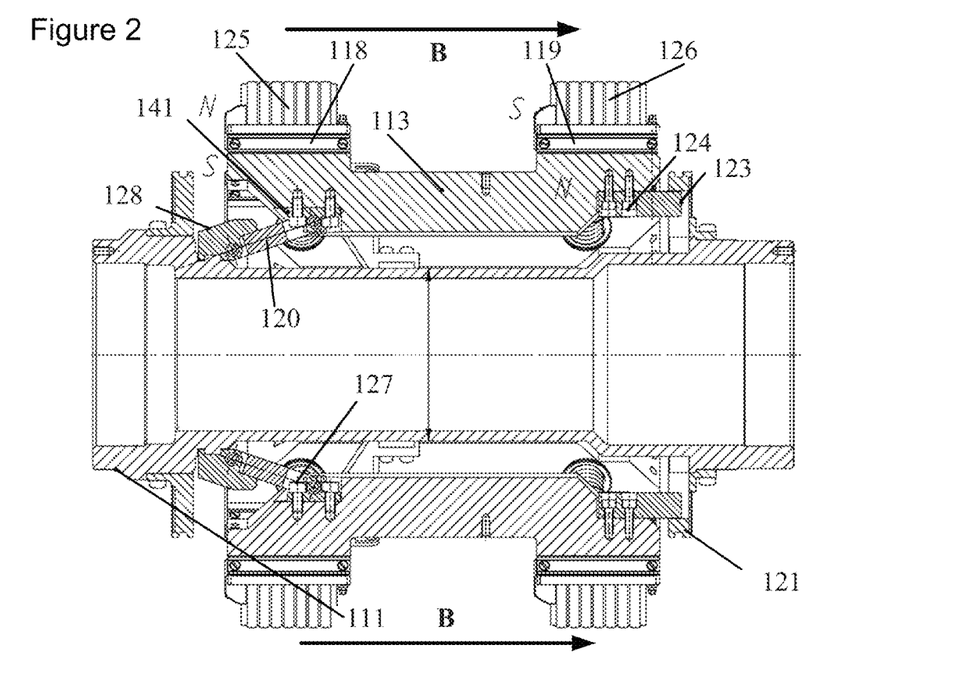
FIG. 2 depicts cross-section of a portion of the tool depicted in FIG. 1.

FIG. 2 depicts an expanded cross-section of a portion of the tool depicted in FIG. 1. The tool contains the housing (111) with axial symmetry. Ferromagnetic bars (113) are installed on the housing (111) around the axis of the housing. An electronic measurement system is installed in the housing (111) and is connected to the EMATs. A power source in the form of a battery is also installed in the housing (111). Permanent magnets (118) and (119) are mounted on each bar (113) and directed by their poles of opposite polarity (shown as "N"—North and "S"—South) towards a direction that will be an internal pipeline surface. In the depicted embodiment, brushes (125) and (126) are mounted on the magnets (118) and (119). "B" shows the direction of the magnetic field. Magnetic flux goes through the pipeline wall.

Figure 3:
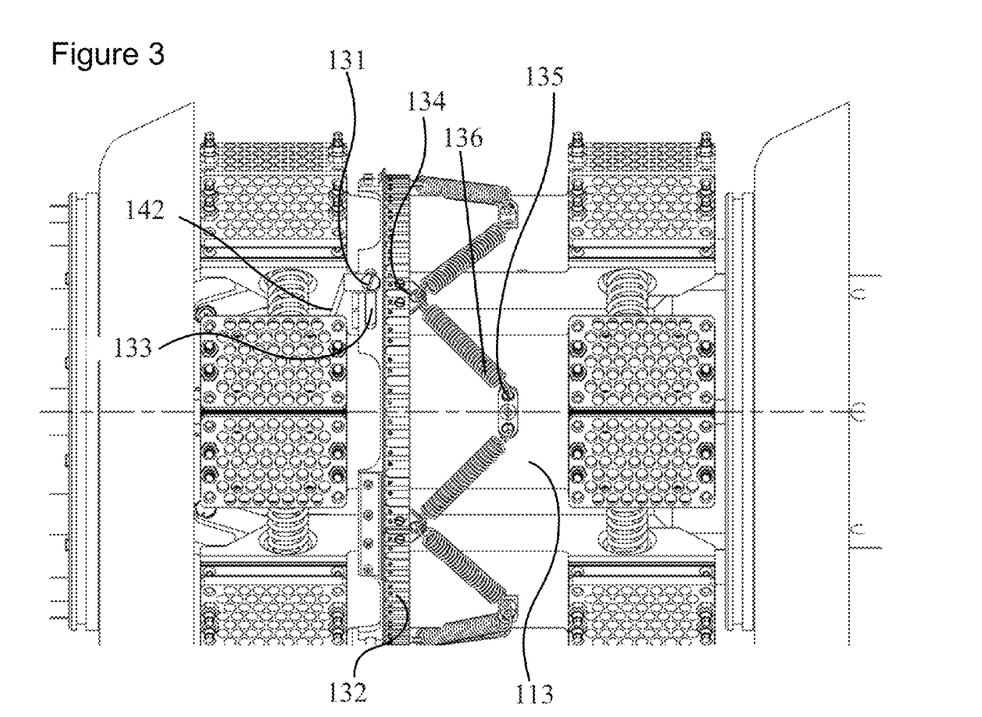
FIG. 3 depicts a further embodiment of the magnet and EMAT belt portion of an EMAT in-line pipeline inspection.

In the depicted embodiment, each bar (113) is connected with the tool housing (111) by means of one lever (120), which is jointed to the front part of the bar (113) by means of joint (141), fixed on the bar (113) via screws (127). The second end of the lever (120) jointed with the arrester (128), fixed on the housing (111). A limit flange (121) is mounted in the rear part of the housing (111). In the alternate outer view of FIG. 3, which depicts one arrangement of EMAT mounts, rods (131) are radially mounted on the housing (111) among the bars (113). EMAT support ring (132) circumscribes the housing (111) and the bars (113). In the depicted embodiment of FIGS. 3 and 4, EMAT support ring (132) is connected with the bars (113) as follows: through holes (133) are disposed on the ring (132) in such a way that the rods (131) go through the holes (133). Limit bracket (142) is fixed on housing (111) by one end and fixed on the peripheral end of rod (131) by other end. EMAT support ring (132) is provided with the ears (134), and each bar (113) is provided with ears (135). EMAT support ring (132) is mounted in such a way that the ears (134) in view on the housing (111) are situated between the neighboring bars (113). Each ear (134) is connected by springs (136) with the ears (135) of two neighboring bars (113), between which the ear (134) is located.

Figure 4:
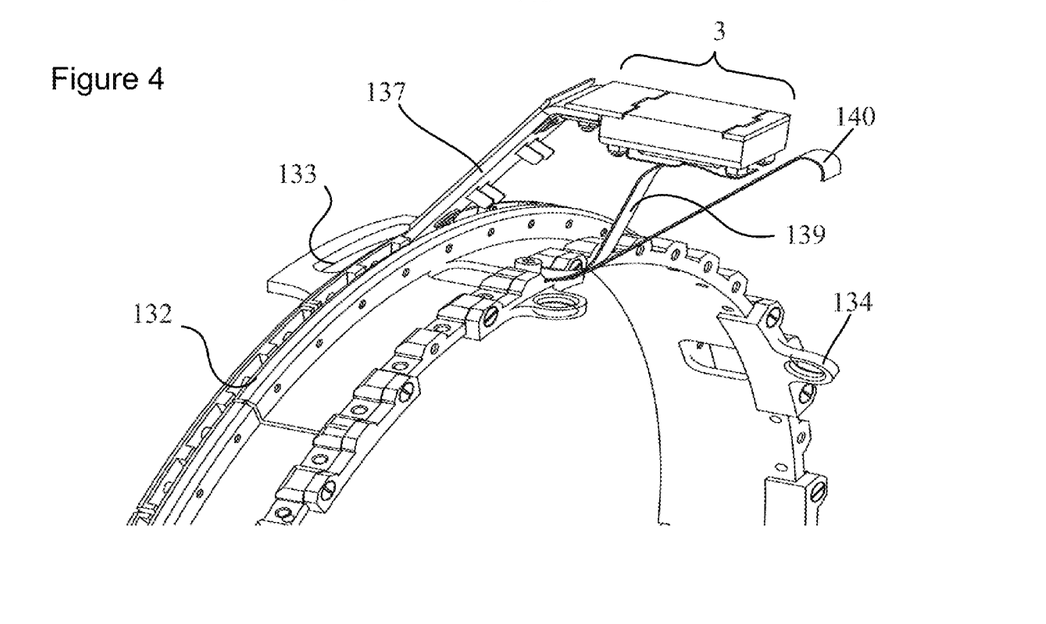
FIG. 4 depicts one embodiment of an EMAT connection to an EMAT connection ring.

In the embodiment depicted in FIG. 4, the individual EMAT housings (4), each including an EMAT coil, are mounted on EMAT support ring (132). The EMAT belt (3) depicted in FIG. 1 is made up of a plurality of individual EMAT housings (4), which may be mounted as depicted in FIG. 4. Each EMAT is connected with the ring (132) by means of elastic plate or arm (137), one end of which is tightly fixed on the EMAT housing, and the second end is tightly fixed on the ring (132). Flat springs (139) and (140) are fixed on the ring (132) and positioned to bias the EMAT housings (4) in close approximation to the pipeline wall.

Figure 5:
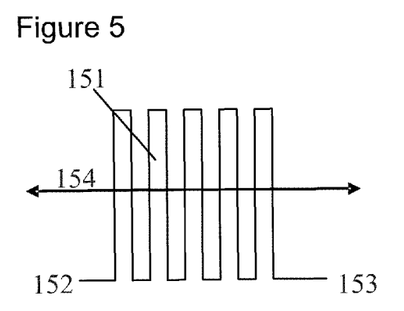
FIG. 5 depicts an EMAT electrical coil.

FIG. 5 figuratively depicts one embodiment of a suitable current coil for an EMAT.

Figure 6:
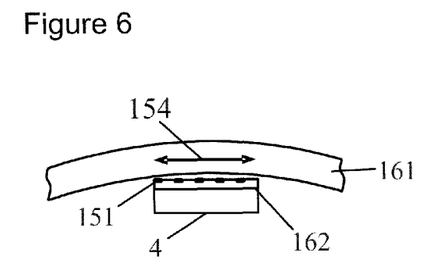
FIG. 6 figuratively depicts a positional relationship between an EMAT and a pipeline wall.
Figure 7:
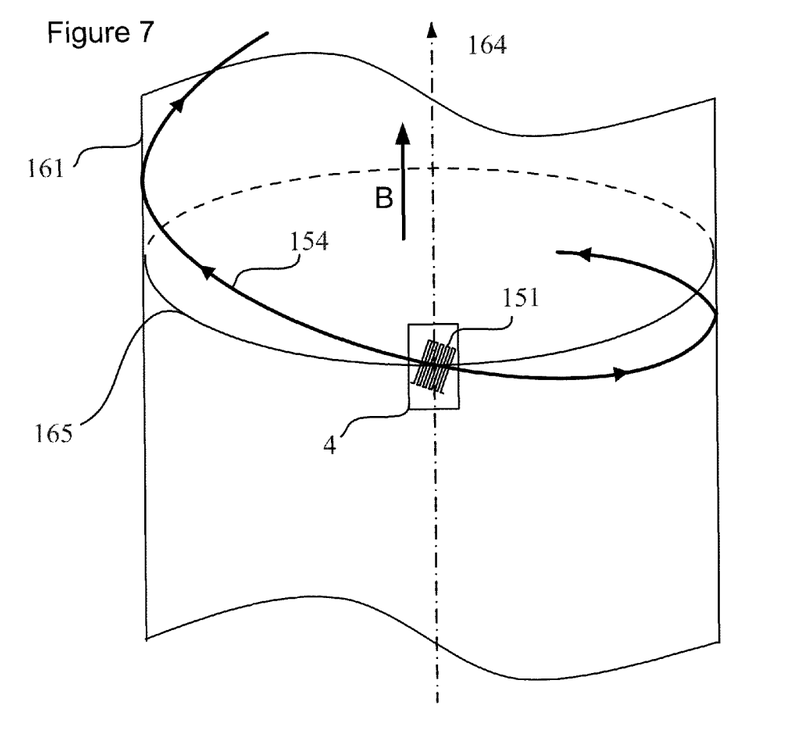
FIG. 7 depicts a direction of propagation of acoustic waves in a pipeline based on the angle of the transmitting EMAT.
Figure 8:
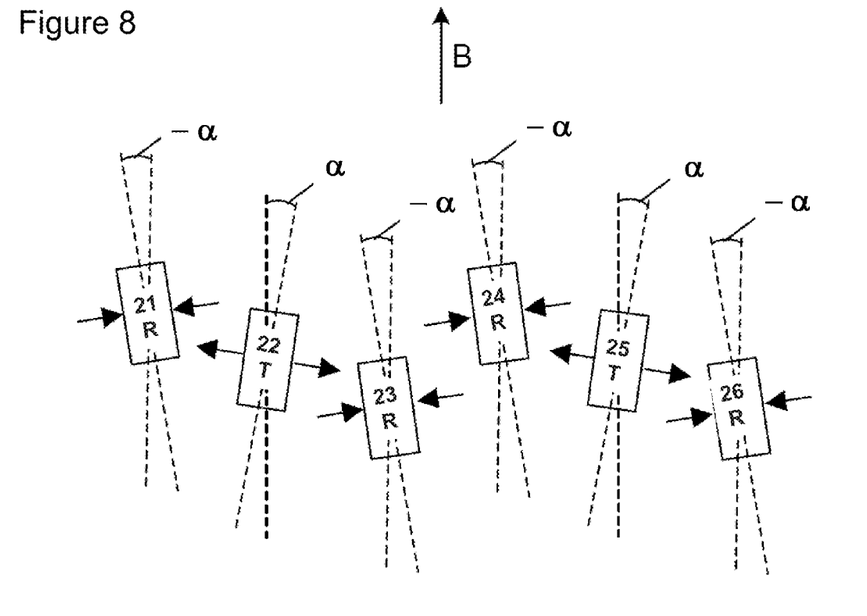
FIG. 8 diagrammatically depicts an arrangement of EMATs in two EMAT R/T clusters according to one embodiment.

Every EMAT includes at least one current coil. In alternative embodiments, two or more coils are included in an EMAT housing and are connected in parallel one to other. The individual coils are oriented in parallel planes and can be realized on the base of multilayer printed plates. In one embodiment double coils are used where two coils are made as metallized tracks on the opposite sides of the printed plate. The depicted coil is a meander coil (151), which is suitable for generating shear waves. Generated shear waves propagate along pipe wall without any slope of the shear waves to pipe wall surface. The angle ($\alpha$) as depicted in FIG. 8 is defined by the coil orientation. Coil current outlets (152) and (153) are connected to an RF generator. As depicted in FIGS. 6 and 7, the plane of meander coil (151) is parallel to the longitudinal axis (164) of pipeline (161). In one embodiment, meander coil (151) is printed on a plate (162) contained within an EMAT housing (4). The meander coil is disposed within each EMAT such that the coil can be closely opposed to an interior surface of the pipeline wall (161).

As depicted in FIGS. 6 and 7, acoustic waves are excited in the wall of pipeline (161) above transmitting EMATs, which include a meander coil (151). Excited waves propagate in directions (154). However, there is an angle between directions (154) and pipeline cross section plane (165). Because of the excited wave propagating at directions (154), which are not circumferential, the excited waves don't circulate in the cross section plane (165) around the longitudinal axis (164) of the pipeline. Instead, according to a novel aspect of the present embodiment, the acoustical waves propagate by helical curves relative to longitudinal pipeline axis (164) and are thus unable to cross over the same receiving EMAT several times.

It is noted that the direction of a magnetic filed at a pipeline wall surface can be expressed in two projections: a linear projection, which is normal to the pipeline wall surface and a planar projection, which is the projection in the plane that is tangential to the pipeline wall surface. Further, the planar projection (which, as aforementioned, is tangential to the pipeline wall surface) can be expressed in two linear projections: a projection that is parallel to the longitudinal axis of the pipeline, and a projection that is tangential to the circumference around the longitudinal axis of the pipeline. In the area of a pipeline wall near the EMATs of EMAT belt (3), the direction of the magnetic filed is tangential to the pipeline wall surface. In the depicted embodiments, the planar projection that is tangential to the circumference around the longitudinal axis of the pipeline is equal to zero, thus making the magnetic filed "B" parallel to the longitudinal axis of the pipeline as depicted in FIG. 7. In an area of pipeline wall near the EMATs of EMAT belt (3), the direction of the acoustic waves (154), generated by the combined action of the magnetic field and the electrical poles of the transmitting EMATs, is tangential to the pipeline wall surface and, within this planar surface, the acoustic waves are at an angle to a tangent to the circumference around the longitudinal axis of the pipeline. The bi-directional helical propagation of the waves is depicted in part in FIG. 7.

For the example shown at FIGS. 5-7, a magnetostriction effect is used. But the arrangement of EMATs and the method is the same for the case when Lorentz forces are used. In one embodiment, the magnetization system of a magnetic flux leakage (MFL) inline inspection tool is used to provide magnetic saturation of ferromagnetic pipeline walls.

The EMAT belt (3) of FIG. 1, is configured to employ a plurality of EMAT R/T clusters, each R/T cluster including two receiving EMATs and one transmitting EMAT disposed between the two receiving EMATs. The transmitting EMAT of the R/T cluster is adapted to generate ultrasound waves in the pipeline wall in two opposite directions, while the paired receiving EMATs in a given R/T cluster are at least partly located in the zone of ultrasound wave propagation that is generated by the transmitting EMAT of the same R/T cluster. As depicted in FIG. 8, the axis of each transmitting EMAT, which is perpendicular to the directions of SH wave emission, is oriented at ($\alpha$) angle to magnetic field direction B. The direction of the magnetic field coincides with the direction of the axis of the tool body and the pipeline axis. The axes of the receiving EMATs, which are perpendicular to directions of SH waves reception, are oriented at ($-\alpha$) angle to magnetic field direction B.

FIG. 8 diagrammatically depicts an arrangement of a two EMAT clusters that form a portion of an EMAT array according to one embodiment. EMA transducers (21R), (22T), (23R) form the first R/T cluster, while EMA transducers (24R), (25T), (26R) form the second depicted R/T cluster. The "T" symbol stands for a transmitting EMAT, while the "R" symbol stands for a receiving EMAT. The arrows outgoing from the transmitting EMATs show directions of ultrasound wave emission. The arrows directed towards receiving EMATs show directions of directional reception of ultrasound waves. Angles between the direction of the magnetic field and the directions of axes perpendicular to directions of emission and reception of ultrasound waves are shown in FIG. 8 as ($\alpha$) and ($-\alpha$) respectively. According to an embodiment, the ($\alpha$) angles are from 3 to 20 degrees while the ($-\alpha$) angles are the corresponding negative angles of $-3$ to $-20$ degrees.

In the depicted embodiment, the centers of transmitting EMAT (22T) and (25T) are located in a transmitting EMAT plane. The centers of receiving EMAT (21R) and (24R) are located in a first receiving EMAT plane, while the centers of receiving EMAT (23R) and (26R) are located in a second receiving EMAT plane. The direction of ultrasound wave emission from the transmitting EMATs is perpendicular to the longitudinal axes of the transmitting EMATs, which longitudinal axes are oriented at a angle to the direction of magnetic field B generated by the pairs of magnets. The axes of the receiving EMAT are perpendicular to directions of ultrasound wave reception, said direction of ultrasound reception being oriented at ($-\alpha$) angle to the direction of the magnetic field.

Figure 9:
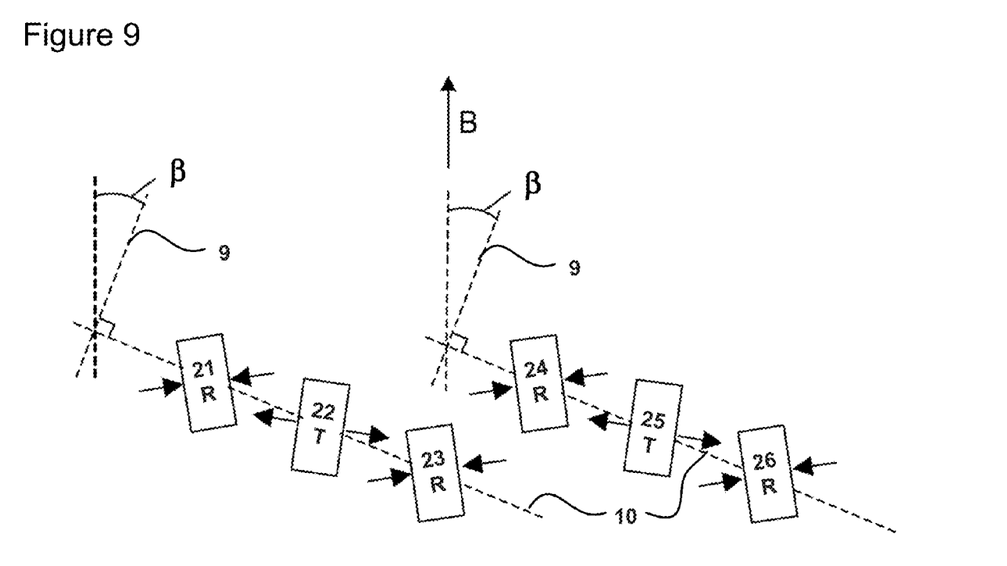
FIG. 9 diagrammatically depicts the linear alignment of EMATs in the EMAT R/T clusters of FIG. 8 as well one embodiment of an angle of the axes of the R/T EMAT clusters to the magnetic field direction.

FIG. 9 depicts an angle ($\beta$), which is between the direction of magnetic field B and an imaginary line that is perpendicular to axis (10). Axis (10) crosses the longitudinal centers of the EMATs in a R/T cluster, which includes one transmitting to two surrounding receiving EMATs. According to this depicted embodiment, wherein the centers of three EMAT in the cluster are positioned on an axis (10) to one another, the line (9) that is perpendicular to line (10) forms a (β) angle with the direction of the magnetic field and the (β) angle is the same for all EMAT R/T clusters.

Figure 10:
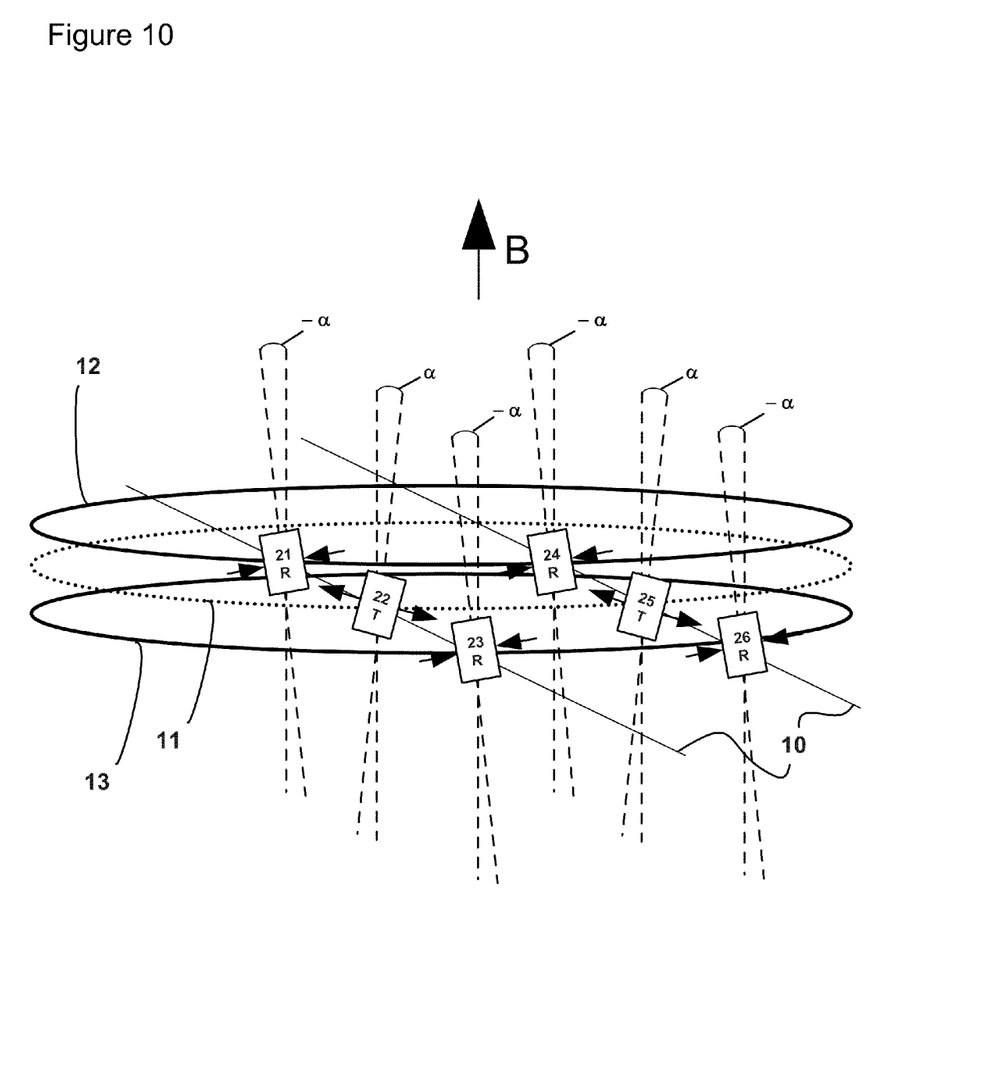
FIG. 10 diagrammatically depicts the planar relationship of transmitting and receiving EMATs in the EMAT belt according to one embodiment.

According to further developments of the first embodiment and as depicted in FIG. 10, the EMATs of a single EMAT belt are arrayed in a series of planes (figuratively depicted as (11), (12), and (13)) around the tool body axis. Of the circumferential belt comprising a plurality of evenly spaced EMAT clusters around the tool body, only two clusters are presented for purposes of depicting the a planar arrangement of receiving and transmitting EMAT. Thus, for illustrative purposes, two EMAT clusters are depicted, one composed of (21R), (22T) and (23R), and a second being composed of (24R), (25T) and (26R). The centers of the transmitting EMAT (22T) and (25T) of the adjacent clusters form a plane (11) that is perpendicular to the tool body axis. The centers of the first receiving EMATs (21R) and (24R) of the adjacent clusters are located in first receiving EMAT plane (12), which is perpendicular to the tool body axis. The centers of the second receiving EMATs (23R) and (26R) of the adjacent clusters form a second receiving EMAT plane (13), which is similarly perpendicular to the tool body axis. The plane of the transmitting EMATs (11) is located between the plane of the first receiving EMATs (12) and the plane of the second receiving EMATs (13). In one aspect, the distance between the plane of transmitting EMATs and each of the planes of receiving EMATs does not exceed the length of the transmitting EMAT in perpendicular direction to the directions of ultrasound wave emission.

Figure 11A:
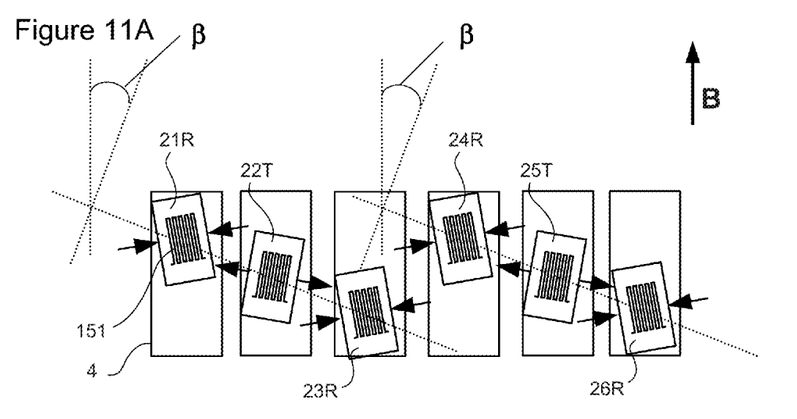
FIG. 11A diagrammatically depicts an arrangement of EMAT coils in two EMAT R/T clusters according to the embodiment depicted in FIGS. 8 and 9.
Figure 11B:
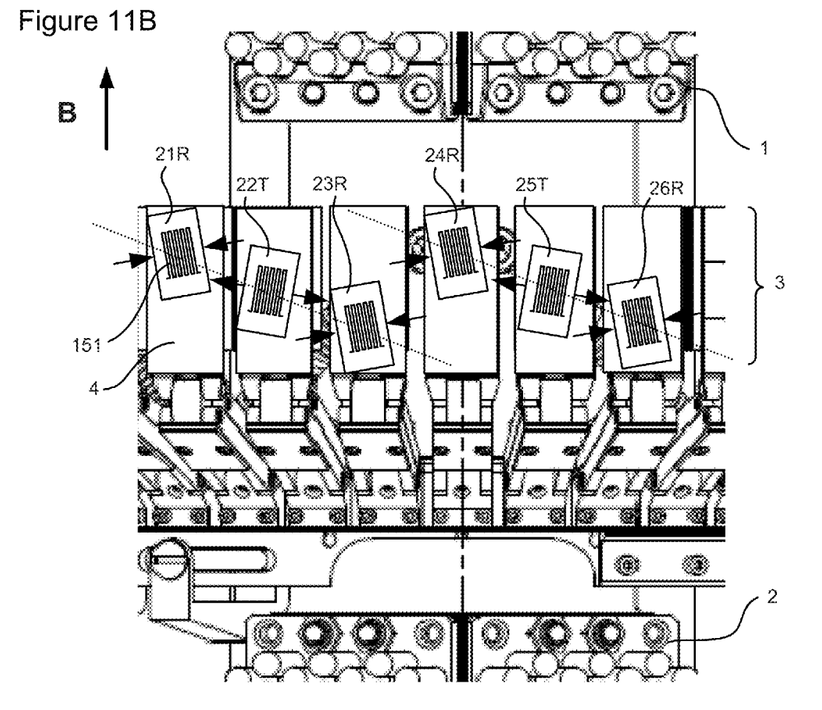
FIG. 11B depicts the EMAT clusters of FIG. 11A overlayed over a section of the tool depicted in FIG. 1.

FIG. 11A diagrammatically depicts the two EMAT clusters of FIGS. 8-10 but also showing the various individual angular placements of receiving and transmitting EMAT current coils (151) within the individual EMAT housings (4). When arrayed in a circumferential ring, these EMATs clusters make up the EMAT belt (3). In FIG. 11B, the EMAT cartoon of FIG. 11A is overlayed over a portion of the in-line pipeline inspection tool depicted in FIG. 1. Thus, FIG. 11B depicts a potential arrangement of R/T EMAT clusters that, together with other clusters that are not depicted, make up EMAT belt (3). The spatial relationship of the EMATs, including integral current coils, to a portion of magnet belts (1) and (2) is shown in the depicted embodiment.

Figure 12A:
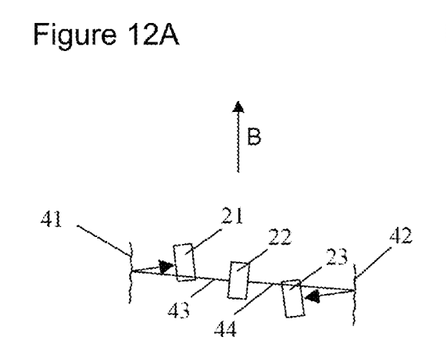
FIGS. 12A and 12B diagram hypothetical reflections of transmitted ultrasonic waves against pipewall cracks and reception by receiving EMATs arrayed in the configuration depicted in FIGS. 8 and 9.
Figure 12B:
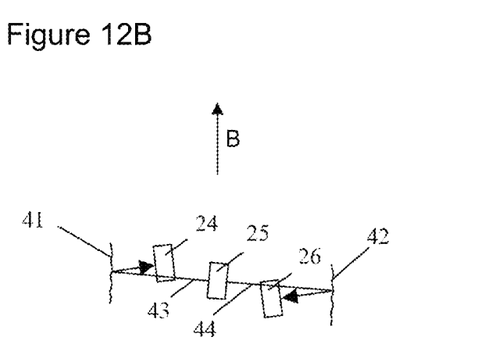

FIG. 12A depicts the path of ultrasound waves (43) and (44) generated by transmitting EMAT (22), which is reflected by defects such as cracks (41) and (42) in a pipewall. The reflected ultrasound waves are received by receiving EMATs (21) and (23). Before it is reflected from crack (41), ultrasound wave (43) can be received by EMAT (21) as a reference wave. Similarly, ultrasound wave (44), before it is reflected from crack (42), can be received by EMAT (23) as a reference wave. FIG. 12B similarly depicts the path of ultrasound waves (43) and (44) generated by transmitting EMAT (25).

In contrast to existing EMAT in-line inspection tools, the disclosed arrangement of EMATs in a given R/T EMAT cluster makes it possible to use the same EMA transducer, e.g., (21) and/or (23), to both receive the initially transmitted ultrasound wave and the wave reflected from the defect. Thus, the initially transmitted ultrasound wave can be used as a reference signal to the reflected wave thus providing an accurate assessment of a given defect. In contrast, in existing EMAT tools where different receivers monitor the transmitted and reflected signals, differences in gaps between the different EMATs and the pipeline wall can cause differences in signals that adversely affect analysis of defects, such as, for example, crack depth determination.

Figure 12C:
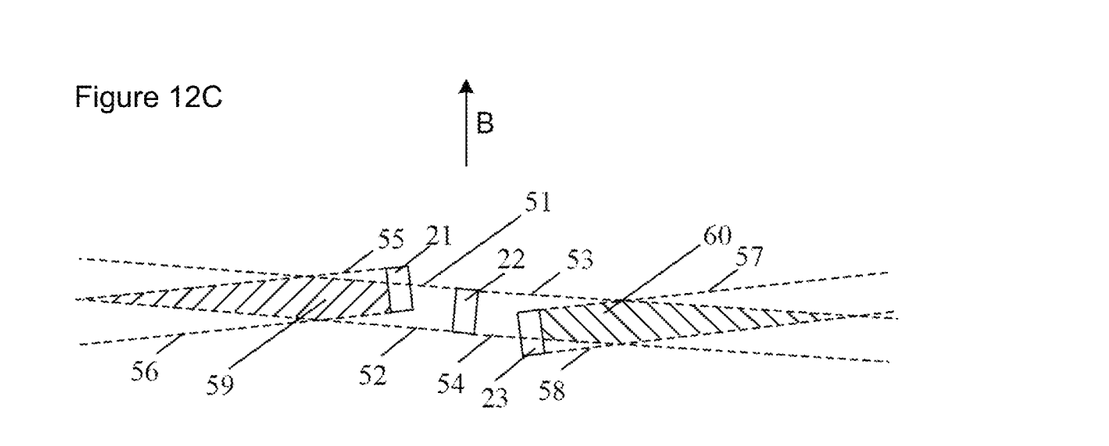
FIG. 12C depicts test areas created by the individual transmitting EMAT (22) of FIG. 8.
Figure 13:
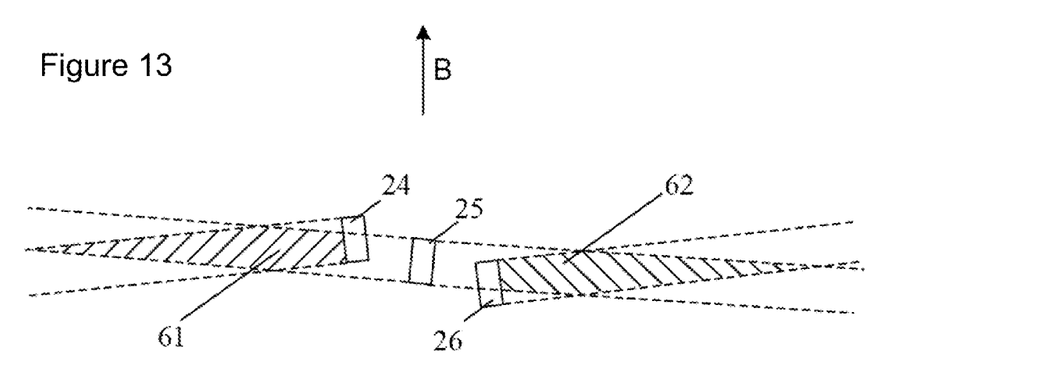
FIG. 13 depicts test areas created by the individual transmitting EMAT (25) of FIG. 8.

FIG. 12C depicts how testing areas (areas of probing) are formed, i.e. on areas of pipeline wall, when R/T cluster of EMAT (21)-(23) is in operation. Lines (51) and (52) depict the restricted propagation zone of ultrasound waves generated by transmitting EMAT (22) in one direction, while lines (53) and (54) depicted the restricted propagation zone of ultrasound waves generated by transmitting EMAT (22) in the opposite direction. Lines (55) and (56) depict the restricted zone of directional reception of reflected ultrasound waves using receiving EMAT (21), while lines (57) and (58) depict the restricted zone of directional reception of reflected ultrasound waves using receiving EMAT (23). The hatched testing area (59) is an area where the ultrasound wave propagation zone restricted by lines (51) and (52) overlaps with the zone of directional reception of reflected ultrasound waves, restricted by lines (55) and (56). Accordingly, hatched testing area (60) is an area where the ultrasound wave propagation zone restricted by lines (53) and (54) overlaps with the zone of directional reception of reflected ultrasound waves, restricted by lines (57) and (58). To depict reflected ultrasound waves that travel from left to right in the plane of the drawing, the hatching is directed from the left bottom corner to the right upper corner, while the reflected ultrasound waves that travel from right to left in the plane of the drawing are depicted by hatching directed from the right bottom corner to the left upper corner. In a similar manner FIG. 13 shows how testing areas (61) and (62) are formed when the R/T cluster of EMAT (24)-(26) is in operation.

Figure 14:
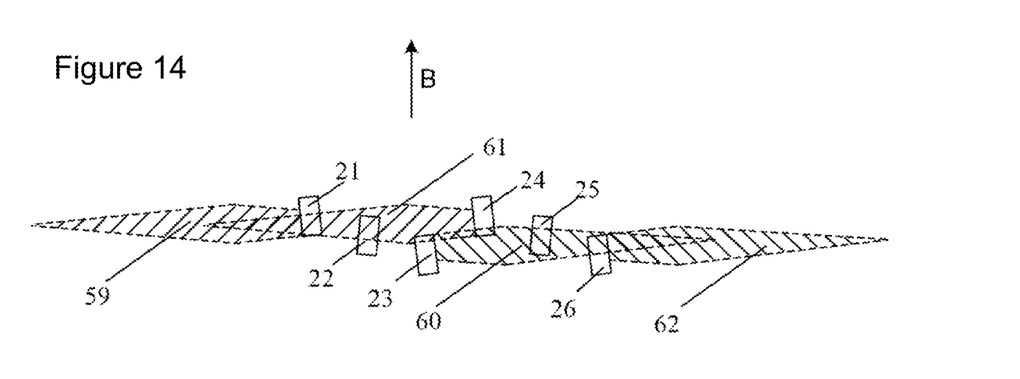
FIG. 14 depicts a pattern of test area overlap when 2 EMAT clusters are arranged according to FIG. 8.

FIG. 14 depicts a conjugation of testing areas of two adjacent EMAT R/T clusters: (21)-(23) and (24)-(26). The drawing shows that testing areas (59) and (61) for the reflected ultrasound waves traveling from left to right in the plane of the drawing are partially overlapped. Testing areas (60) and (62) for the reflected ultrasound waves traveling from right to left in the plane of the drawing are similarly partially overlapped. Formation of an array of EMAT R/T clusters from the mentioned groups makes it possible to probe the whole circumference of the pipe in both directions, i.e. clockwise and anticlockwise.

Example 2

In an alternative embodiment, an in-line inspection tool for inspecting pipeline wall for defects is provided that includes the body with axial symmetry and means of tool control and processing of measurement data. The tool further includes a pipe wall magnetization element fitted on the body that includes pairs of magnets facing the internal surface of a pipe by the poles of opposite polarity as well as EMATs installed in-between said poles. The magnetization element and the EMATs are adapted to come in close approximation to the internal surface of the pipeline and may press lightly against the internal surface or depart slightly from the surface while the inspection tool travels through a pipeline. The EMAT are arranged in EMAT clusters wherein each cluster includes two receiving EMATs and one transmitting EMAT located between said receiving EMATs. The transmitting EMAT is capable of generating ultrasound waves in pipeline wall in two opposite directions, while the receiving EMAT in the cluster are projected on the pipeline wall in an area at least partly located in the zone of ultrasound wave propagation generated by the transmitting EMAT.

Figure 15:
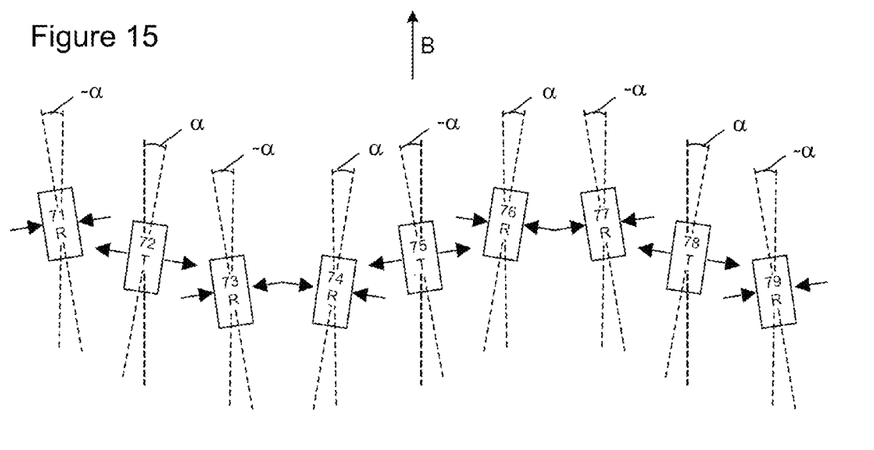
FIG. 15 diagrammatically depicts an arrangement of EMATs in EMAT R/T clusters according to an alternate embodiment.

According to one development of the second embodiment as graphically depicted in FIG. 15, for adjacent clusters, an angle between an axis perpendicular to a line that crosses the centers of the receiving EMAT in a given cluster and the direction of magnetic field, is equal in magnitude but opposite in sign to the corresponding angle for the adjacent cluster. That is, an axis perpendicular to the direction of ultrasound waves emitted from a given transmitting EMAT is oriented at α angle to the direction of said magnetic field, while an axis that is perpendicular to the direction of ultrasound waves emitted by the transmitting EMAT of each adjacent group is oriented at −α angle to the direction of said magnetic field. FIG. 15 depicts a three cluster portion of a circumferential belt of EMATs. EMATs (71), (72), and (73) form a first cluster, EMATs (74), (75), and (76) form the second cluster, while EMATs (77), (78), and (79) form the third cluster. As before, the "T" symbols stand for transmitting EMAT while the "R" symbols stand for receiving EMAT. The direction of magnetic field B coincides with the direction of tool body axis and pipeline axis.

The arrows outgoing from the EMAT show directions of ultrasound wave emission. Arrows directed towards EMAT show the directional reception of ultrasound waves by receiving EMAT. Angles between the direction B of the magnetic field and directions of axes that are perpendicular to the directions of emission and reception of ultrasound waves are shown in FIG. 15 as (α) and (−α) respectively. The centers of transmitting EMAT (72), (75) and (78) are located in a plane of transmitting EMAT, the centers of receiving EMAT (71), (76), and (77) are located in a plane of the first receiving EMATs, and the centers of receiving EMAT (73), (74), and (79) are located in a plane of the second receiving EMATs. The plane of transmitting EMATs is located between the planes of receiving EMATs and a distance between the plane of transmitting EMAT and each of the planes of receiving EMAT does not exceed the length of the transmitting EMAT in perpendicular direction to the directions of ultrasound wave emission.

Figure 16:
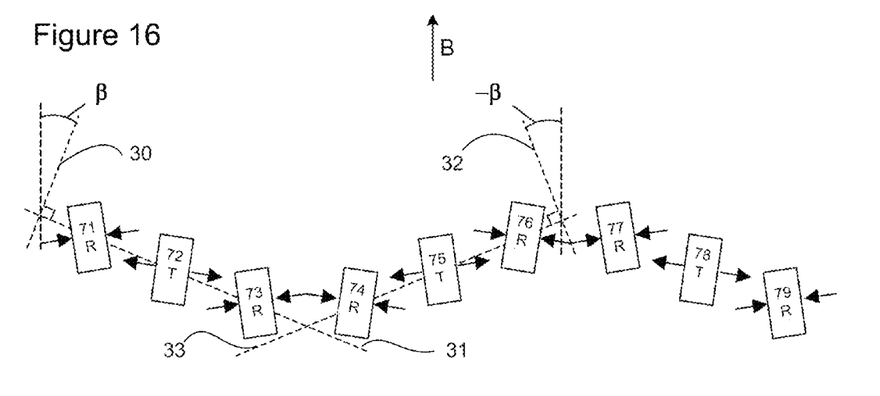
FIG. 16 diagrammatically depicts the linear alignment of EMATs in the EMAT R/T clusters of FIG. 15 as well one embodiment of the angles of the various axes of R/T EMAT clusters to the magnetic field direction.

FIG. 16 depicts the angle (β) between the direction of magnetic field B and the line (30) that is perpendicular to the axis (31) that crossing the centers of EMATs (71)-(73) as a cluster and angle (−β) between the direction of magnetic field B and the line (32) that is perpendicular to an axis (33) that crosses the centers of the adjacent cluster of EMAT (74)-(76). For the cluster of EMAT (77)-(79), the angle between the direction of magnetic field B and the line perpendicular to the axis that crosses the centers of the EMATs is also β.

Figure 17:
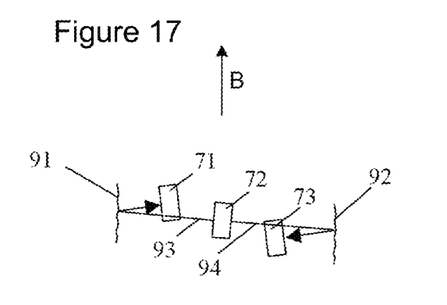
FIGS. 17 and 18 diagram hypothetical reflections of transmitted ultrasonic waves against pipewall cracks and reception by receiving EMATs according to an embodiment as depicted in FIG. 15.
Figure 18:
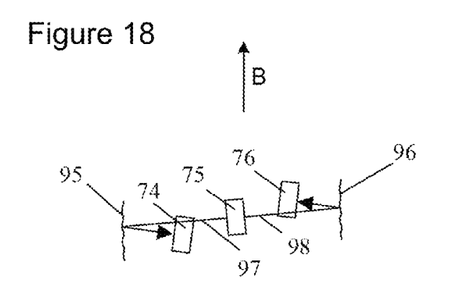

FIG. 17 depicts the paths of ultrasound waves (93) and (94), generated by EMAT (72), which are reflected by defects such as cracks (91) and (92) and received by receiving EMATs (71) and (73). Likewise, FIG. 18 shows the path of ultrasound waves (97) and (98), generated by transmitting EMAT (75), which are reflected by defects (95) and (96) and received by receiving EMATs (74) and (76).

Figure 19:
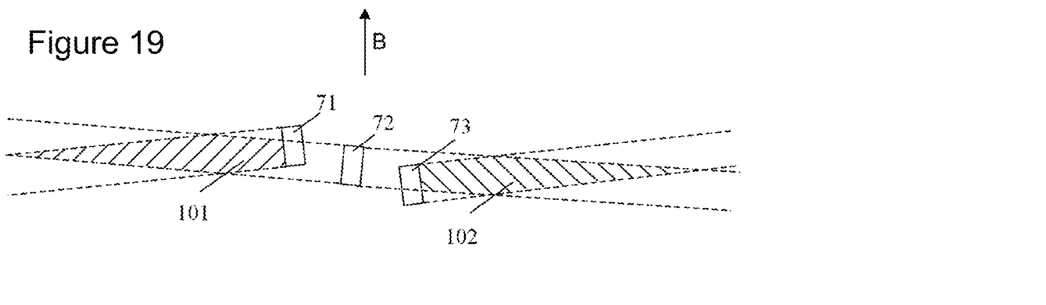
FIGS. 19-21 depict test areas created by the individual transmitting EMATs of FIG. 15.
Figure 20:
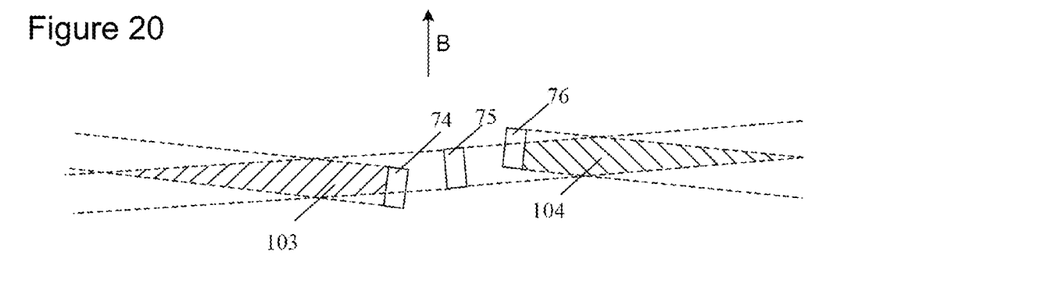
Figure 21:
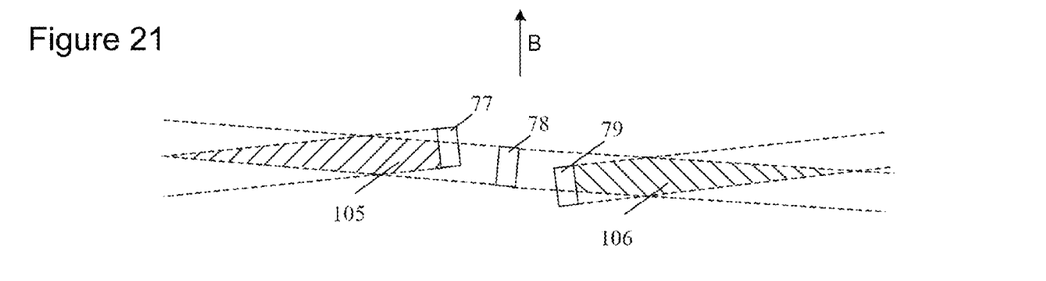

FIG. 19 depicts how testing areas (101) and (102) are formed when EMAT R/T cluster (71)-(73) are in operation. Likewise FIG. 20 depicts how testing areas (103) and (104) are formed when EMAT R/T cluster (74)-(76) is in operation and FIG. 21 depicts how testing areas (105) and (106) are formed when EMAT R/T cluster (77)-(79) is in operation. The testing areas have hatching. For reflected ultrasound waves traveling from left to right in the plane of the drawing the hatching is directed from the left bottom corner to the right upper corner, for reflected ultrasound waves traveling from right to left in the plane of the drawing the hatching is directed from the right bottom corner to the left upper corner.

Figure 22:
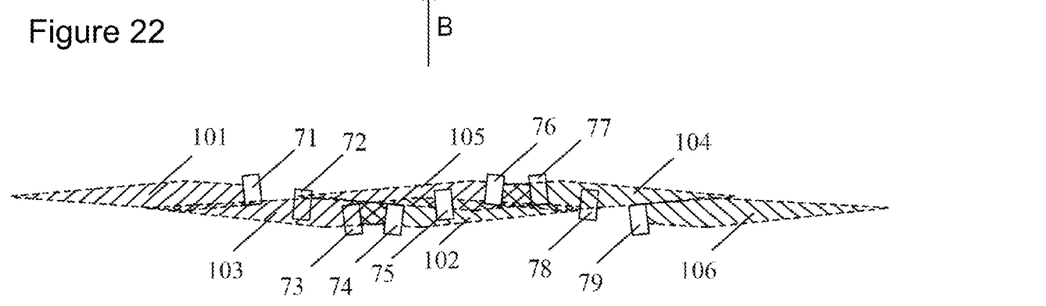
FIG. 22 depicts a pattern of test area overlap when 3 EMAT clusters are arranged according to FIG. 15.

FIG. 22 shows conjugation of testing areas of three adjacent clusters of EMAT: (71)-(73), (74)-(76) and (77)-(79). The drawing shows that testing areas (101), (103), and (105) are partially overlapped for the reflected ultrasound waves traveling from left to right in the plane of the drawing. Testing areas (102), (104), and (106) are also partially overlapped for the reflected ultrasound waves traveling from right to left in the plane of the drawing. Therefore, a belt of EMAT that includes the mentioned groups is able to probe the whole circumference of the pipe in both directions, i.e. clockwise and anticlockwise.

An additional feature of this embodiment is that receiving EMAT (73) is directed with one side towards transmitting EMAT (75), which belongs to an adjacent R/T EMAT cluster. Similarly receiving EMAT (74) is directed with one side towards transmitting EMAT (72) of the adjacent R/T EMAT cluster, receiving EMAT (76) is directed with one side towards transmitting EMAT (78) of the adjacent cluster, and receiving EMAT (77) is directed with one side towards transmitting EMAT (75) of the adjacent cluster. As a consequence, EMAT (73) is able to receive an initial ultrasound wave from transmitting EMAT (75) as a reference wave and, thus act as a reference EMAT to the adjacent cluster. Similarly, EMAT (74) can receive an initial ultrasound wave from transmitting EMAT (72), EMAT (76) can receive an initial ultrasound wave from transmitting EMAT (78), and EMAT (77) can receive an initial ultrasound wave from transmitting EMAT (75).

The disclosed dual use of a receiving EMAT as receiving EMAT and reference EMAT is particularly useful in crack depth determination. Certain prior art EMAT tools such as that disclosed in CA2592094, have utilized reference EMATs in order to determine amplitude ratio and hence crack depth. However, the present EMAT inspection tool provides for internal referencing that improves crack depth determination. While EMAT (73) can receive initial ultrasound waves transmitted by EMAT (72) and subsequently the waves reflected from crack, during another time period EMAT (73) can receive initial ultrasound wave from transmitting EMAT (75) but in this case the initial ultrasound wave from transmitting EMAT (72) or from transmitting EMAT (75) is a reference wave and EMAT (73) is acting as a reference EMAT. Thus, in such embodiments a special reference EMATs is not required because a given receiving EMATs can serve as reference EMATs at some time periods while serving as receiving EMATs that receive reflected waves during different time periods.

The principle can be explained as follows. If a transmitted acoustic wave is reflected from a crack, the amplitude of the reflected wave is less then the amplitude of the transmitted wave. And the reflected/transmitted wave amplitude ratio depends on the crack depth. For this reason, in order to determine the crack depth, it has been heretofore necessary to receive transmitted acoustic waves before reflecting from the crack by the first receiving EMAT and to measure the amplitude of this signal. This signal from EMAT can be called a reference signal and this receiving EMAT can be called a reference EMAT. Following receipt of the reference signal, it was necessary to receive the acoustic wave reflected from the crack by another receiving EMAT and measure its amplitude. The ratio of the amplitudes provided the information about the crack depth. Because waves propagate in pipeline wall while the EMATs are disposed near the wall, receiving the waves before reflecting doesn't affect further propagation and the amplitude of the acoustic wave. However, the amplitude of electrical signal from receiving EMATs depends both from the amplitude of acoustic wave and from the gap between receiving EMAT and pipeline wall. Increasing of the gap suppresses the amplitude of the electrical signal. Thus, if the transmitted wave and the reflected wave are received by different receiving EMATs having different gaps, the reflected/transmitted wave amplitude ratio will be false and the determined crack depth will also be false.

In certain aspects, the aforementioned problem is solved by providing that the transmitted acoustic wave and the reflected acoustic wave can be received by the same EMAT. In this case, the gap will suppress both the signal from transmitted wave and the signal from reflected wave equally. So reflected/transmitted wave amplitude ratio will not depend on the gap and hence determined crack depth will be more accurate.

In some embodiments, the accuracy of the crack depth determination is provided through the use of acoustic waves propagating in the pipeline wall clockwise, together with determinations made from acoustic waves propagating in the pipeline wall anticlockwise. Comparing the ratio values from clockwise acoustic waves and from anticlockwise acoustic waves for the same crack is employed to confirm the correctness of the determined crack depth if the two compared values are similar.

In one embodiment the ($\alpha$) angle is from 3 to 20 degrees and the centers of the three EMAT in a cluster in line with one another. For each cluster, the axes of the receiving EMAT in the cluster that are perpendicular to directions of ultrasound wave reception are inclined to the direction of said magnetic field at an angle which is equal in magnitude but opposite in sign to the angle between the axis of the transmitting EMAT, which is perpendicular to directions of ultrasound waves emission, and the direction of said magnetic field.

All publications, patents and patent applications cited herein are hereby incorporated by reference as if set forth in their entirety herein. While the inventions disclosed herein have been described with reference to illustrative embodiments, this description is not intended to be construed in a limiting sense. Various modifications and combinations of illustrative embodiments, as well as other embodiments, will be apparent to persons skilled in the art upon reference to the description. It is therefore intended that the appended claims encompass such modifications and enhancements.

I claim:

1. An in-line electromagnetic acoustic transducer (EMAT) pipeline inspection tool comprising:
    a tool body having mounted thereon at least one pipewall magnetization element and at least one EMAT belt, wherein the EMAT belt comprises a plurality of individual EMAT receiving/transmitting (R/T) clusters arranged circumferentially around the tool body, each EMAT cluster including one transmitting EMAT disposed between paired receiving EMATs;
    wherein the magnetization element is adapted to generate a magnetic field (B) whose orientation coincides with a direction of a longitudinal axis of the pipeline and a longitudinal axis of tool body; and
    wherein the EMATs in a given R/T cluster are centered on a linear axis that is on an angle ($\beta$) to the direction of the magnetic field (B) and a line that is perpendicular to the linear axis while the EMATs in an adjacent R/T cluster are centered on a linear axis that is at an angle ($-\beta$) to the direction of the magnetic field (B) and a line that is perpendicular to the linear axis.

2. The in-line EMAT pipeline inspection tool of claim 1 wherein the transmitting EMAT of an individual EMAT R/T cluster is adapted to generate ultrasound waves in the pipeline wall in two opposite directions.

3. The in-line EMAT pipeline inspection tool of claim 1 wherein the paired receiving EMATs in an individual R/T EMAT cluster are at least partly located in a zone of ultrasound wave propagation that is generated by the transmitting EMAT of the individual R/T EMAT cluster.

4. The in-line EMAT pipeline inspection tool of claim 1 wherein the pipewall magnetization element comprises two belts of paired magnets having poles of polarity facing an internal surface of the pipewall, each of the two belts populated by paired magnets of opposite polarity to those of the other belt of magnets.

5. The in-line EMAT pipeline inspection tool of claim 1, wherein the EMAT belt is disposed in-between the belts of magnets of opposite polarity.

6. The in-line EMAT pipeline inspection tool of claim 1, wherein the EMATs of an individual cluster are arranged to enable a single receiving EMAT to monitor both an initially transmitted ultrasound wave sent from the transmitting EMAT and a corresponding returning reflection from a pipewall defect, thereby providing each signal with its own internal reference.

7. The in-line EMAT pipeline inspection tool of claim 1, wherein the transmitting EMAT in a cluster is capable of generating ultrasound waves in pipeline wall in two opposite directions and at least one receiving EMAT in the cluster is projected on the pipewall in an area at least partly located in a zone of ultrasound wave propagation generated by the transmitting EMAT.

8. The in-line EMAT pipeline inspection tool of claim 1, wherein the transmitting EMATs have longitudinal axes that are perpendicular to a direction of ultrasound wave emission and wherein the transmitting EMAT longitudinal axes are oriented at an angle ($\alpha$) to the orientation of magnetic field (B), angle ($\alpha$) being from 3 to 20 degrees.

9. The in-line EMAT pipeline inspection tool of claim 8 wherein the receiving EMATs, have longitudinal axes which are perpendicular to a direction of ultrasound wave reception and wherein the receiving EMAT longitudinal axes are oriented at an angle ($-\alpha$) to the orientation of magnetic field (B), angle ($\alpha$) being from 3 to 20 degrees.

10. The in-line EMAT pipeline inspection tool of claim 1, wherein at least one receiving EMAT from a given R/T cluster is directed with one side towards a transmitting EMAT belonging to an adjacent R/T EMAT cluster, thus permitting said receiving EMAT to receive an initial ultrasound wave from the transmitting EMAT of the adjacent cluster and act as a reference EMAT to the adjacent cluster.

11. An in-line electromagnetic acoustic transducer (EMAT) pipeline inspection tool comprising:
    a tool body having mounted thereon at least one pipewall magnetization element and at least one EMAT belt, wherein the EMAT belt comprises a plurality of individual EMAT receiving/transmitting (R/T) clusters arranged circumferentially around the tool body, each EMAT cluster including one transmitting EMAT disposed between paired receiving EMATs;
    wherein:
        the EMATs of an individual cluster are arranged to enable a single receiving EMAT to monitor both an initially transmitted ultrasound wave sent from the transmitting EMAT and a corresponding returning reflection from a pipewall defect, thereby providing each signal with its own internal reference;
        the magnetization element is adapted to generate a magnetic field (B) whose orientation coincides with a direction of a longitudinal axis of the pipeline and a longitudinal axis of tool body; and
        the transmitting EMATs have longitudinal axes that are perpendicular to a direction of ultrasound wave emission and wherein the transmitting EMAT longitudinal axes are oriented at an angle ($\alpha$) to the orientation of magnetic field (B), angle ($\alpha$) being from 3 to 20 degrees.

12. The in-line EMAT pipeline inspection tool of claim 11 wherein the transmitting EMAT of an individual EMAT R/T cluster is adapted to generate ultrasound waves in the pipeline wall in two opposite directions.

13. The in-line EMAT pipeline inspection tool of claim 11 wherein the paired receiving EMATs in an individual R/T EMAT cluster are at least partly located in a zone of ultrasound wave propagation that is generated by the transmitting EMAT of the individual R/T EMAT cluster.

14. The in-line EMAT pipeline inspection tool of claim 11 wherein the pipewall magnetization element comprises two belts of paired magnets having poles of polarity facing an internal surface of the pipewall, each of the two belts populated by paired magnets of opposite polarity to those of the other belt of magnets.

15. The in-line EMAT pipeline inspection tool of claim 11, wherein the EMAT belt is disposed in-between the belts of magnets of opposite polarity.

16. The in-line EMAT pipeline inspection tool of claim 11, wherein the transmitting EMAT in a cluster is capable of generating ultrasound waves in pipeline wall in two opposite directions and at least one receiving EMAT in the cluster is projected on the pipewall in an area at least partly located in a zone of ultrasound wave propagation generated by the transmitting EMAT.

17. The in-line EMAT pipeline inspection tool of claim 11 wherein the receiving EMATs, have longitudinal axes which are perpendicular to a direction of ultrasound wave reception and wherein the receiving EMAT longitudinal axes are oriented at an angle ($-\alpha$) to the orientation of magnetic field (B), angle ($\alpha$) being from 3 to 20 degrees.

18. The in-line EMAT pipeline inspection tool of claim 11, wherein the EMATs in the R/T cluster are centered on a linear axis and the linear axis is at an angle ($\beta$) to the direction of the magnetic field (B) and a line that is perpendicular to the linear axis.

19. The in-line EMAT pipeline inspection tool of claim 18, wherein the ($\beta$) angle is the same for all EMAT R/T clusters in the EMAT belt.

20. An in-line electromagnetic acoustic transducer (EMAT) pipeline inspection tool comprising:
a tool body having mounted thereon at least one pipewall magnetization element and at least one EMAT belt, wherein the EMAT belt comprises a plurality of individual EMAT receiving/transmitting (R/T) clusters arranged circumferentially around the tool body, each EMAT cluster including one transmitting EMAT disposed between paired receiving EMATs;
wherein the magnetization element is adapted to generate a magnetic field (B) whose orientation coincides with a direction of a longitudinal axis of the pipeline and a longitudinal axis of tool body; and
wherein the transmitting EMATs have longitudinal axes that are perpendicular to a direction of ultrasound wave emission and wherein the transmitting EMAT longitudinal axes are oriented at an angle ($\alpha$) to the orientation of magnetic field (B), angle ($\alpha$) being from 3 to 20 degrees.

21. The in-line EMAT pipeline inspection tool of claim 20 wherein the transmitting EMAT of an individual EMAT R/T cluster is adapted to generate ultrasound waves in the pipeline wall in two opposite directions.

22. The in-line EMAT pipeline inspection tool of claim 20 wherein the paired receiving EMATs in an individual R/T EMAT cluster are at least partly located in a zone of ultrasound wave propagation that is generated by the transmitting EMAT of the individual R/T EMAT cluster.

23. The in-line EMAT pipeline inspection tool of claim 20 wherein the pipewall magnetization element comprises two belts of paired magnets having poles of polarity facing an internal surface of the pipewall, each of the two belts populated by paired magnets of opposite polarity to those of the other belt of magnets.

24. The in-line EMAT pipeline inspection tool of claim 20, wherein the EMAT belt is disposed in-between the belts of magnets of opposite polarity.

25. The in-line EMAT pipeline inspection tool of claim 20, wherein the transmitting EMAT in a cluster is capable of generating ultrasound waves in pipeline wall in two opposite directions and at least one receiving EMAT in the cluster is projected on the pipewall in an area at least partly located in a zone of ultrasound wave propagation generated by the transmitting EMAT.

26. The in-line EMAT pipeline inspection tool of claim 20 wherein the receiving EMATs, have longitudinal axes which are perpendicular to a direction of ultrasound wave reception and wherein the receiving EMAT longitudinal axes are oriented at an angle ($-\alpha$) to the orientation of magnetic field (B), angle ($\alpha$) of the transmitting EMATs being from 3 to 20 degrees.

27. The in-line EMAT pipeline inspection tool of claim 20, wherein the EMATs in the R/T cluster are centered on a linear axis and the linear axis is at an angle ($\beta$) to the direction of the magnetic field (B) and a line that is perpendicular to the linear axis.

28. The in-line EMAT pipeline inspection tool of claim 27, wherein the ($\beta$) angle is the same for all EMAT R/T clusters in the EMAT belt.

* * * * *